United States Patent
Ashworth et al.

(10) Patent No.: US 6,664,249 B1
(45) Date of Patent: Dec. 16, 2003

(54) BICYCLIC VASOPRESSIN AGONISTS

(75) Inventors: Doreen Mary Ashworth, Southhampton (GB); Gary Robert William Pitt, Tidworth (GB); Peter Hudson, Southampton (GB); Christopher Martyn Yea, Romsey (GB); Richard Jeremy Franklin, Wokingham (GB)

(73) Assignee: Ferring BV, Hoofddorf (NL)

( * ) Notice: Subject to any disclaimer, the term of this patent is extended or adjusted under 35 U.S.C. 154(b) by 0 days.

(21) Appl. No.: 10/111,007

(22) PCT Filed: Oct. 20, 2000

(86) PCT No.: PCT/GB00/04055

§ 371 (c)(1),
(2), (4) Date: Jun. 10, 2002

(87) PCT Pub. No.: WO01/29005

PCT Pub. Date: Apr. 26, 2001

(30) Foreign Application Priority Data

Oct. 20, 1999 (GB) .............................. 9924836

(51) Int. Cl.$^7$ .............................. A01N 43/00
(52) U.S. Cl. .............................. 514/211.09; 514/211.1; 514/212.01; 514/215; 514/217.01; 514/221; 540/491; 540/492; 540/521; 540/523
(58) Field of Search .............................. 540/491, 492, 540/521, 523; 514/211.09, 211.1, 215, 217.01, 212.01, 221

(56) References Cited

U.S. PATENT DOCUMENTS

| 5,677,299 A | 10/1997 | Ogawa et al. | |
|---|---|---|---|
| 5,753,644 A | 5/1998 | Ogawa et al. | |
| 5,753,677 A | * 5/1998 | Ogawa et al. | .............. 514/311 |

FOREIGN PATENT DOCUMENTS

| EP | 0 514 667 A1 | 11/1992 |
|---|---|---|
| WO | WO 91/05549 A1 | 5/1991 |
| WO | WO 94/12476 A1 | 6/1994 |
| WO | 94/12476 * | 6/1994 |
| WO | WO 94/20473 A1 | 9/1994 |

OTHER PUBLICATIONS

Yanagisawa, "Tetrahydrobenzazepine Derivative," Patent Abstracts of Japan, vol. 018, No. 140, Mar. 8, 1994, JP 05–320135, Dec. 3, 1993, 1 Sheet, Abstract.

Yabuuchi, "Pharmaceutical Composition," Patent Abstracts of Japan, vol. 1999, No. 08, Jun. 30, 1999, JP 11–060488, Mar. 12, 1999, 1 Sheet, Abstract.

* cited by examiner

*Primary Examiner*—D. Margaret Seaman
(74) *Attorney, Agent, or Firm*—Foley & Lardner

(57) ABSTRACT

Compounds according to general formula (1), and pharmaceutically acceptable salts thereof, wherein V is a covalent bond or NH, X is selected from $CH_2$, O and N-alkyl, Z is either S or —CH=CH—, $R^1$ and $R^2$ are independently selected from H, F, Cl, Br and alkyl, $R^3$ is selected from OH, O-alkyl and $NR^4R^5$, $R^4$ and $R^5$ are each independently H or alkyl, or together are —$(CH_2)_q$—, p is 0, 1, 2, 3 or 4, and q is 4 or 5, are new. They are agonists at the asopressin $V_2$ receptor and are useful as antidiuretics and pro-coagulants.

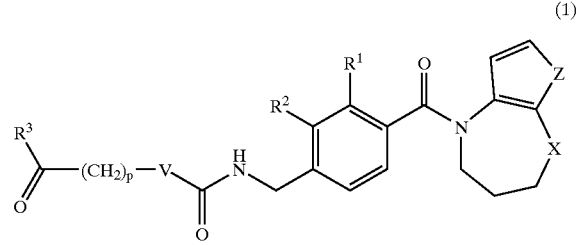

(1)

17 Claims, No Drawings

BICYCLIC VASOPRESSIN AGONISTS

FIELD OF INVENTION

This application is a 371 of PCT/GB00/04055, filed Oct. 20, 2000. The present invention relates to a class of novel chemical entities which act as agonists of the peptide hormone vasopressin. They reduce urine output from the kidneys and so are useful in the treatment of certain human diseases characterised by polyuria. They are also useful in the control of urinary incontinence and bleeding disorders.

BACKGROUND TO THE INVENTION

Vasopressin is a peptide hormone secreted by the posterior pituitary gland. It acts on the kidney to increase water retention and so reduce urine output. For this reason, vasopressin is alternatively known as "antidiuretic hormone". It also acts on the vasculature, where it produces a hypertensive effect. The cellular receptors that mediate these two actions have been characterised and shown to be different. The antidiuretic action is mediated by the type-2 vasopressin receptor, commonly called the $V_2$ receptor. Agents that can interact with the $V_2$ receptor and activate it in the same way as vasopressin are called $V_2$ receptor agonists (or simply $V_2$ agonists). Such agents will have an antidiuretic action. If these agents interact selectively with the $V_2$ receptor and not the other vasopressin receptor subtypes, then they will not have the hypertensive effect of vasopressin. This would be an important safety consideration and make such agents attractive for the treatment of human disease conditions characterised by polyuria (which is herein taken to mean excessive urine production).

Minirin™, DDAVP™) is a peptide analogue of vasopressin which is selectively an agonist at the $V_2$ receptor. It is used in the treatment of central diabetes insipidus, which is a condition that results from defective secretion of vasopressin. It is also employed in the control of nocturnal enuresis and may also be of use in the control of nocturia. However, desmopressin is not an ideal agent in all respects. Even the best current syntheses of the agent are lengthy, and desmopressin is not amenable to the most convenient of purification techniques such as crystallisation. Consequently, desmopressin is relatively expensive. It has a very low oral bioavailability, and there is some variability in this parameter.

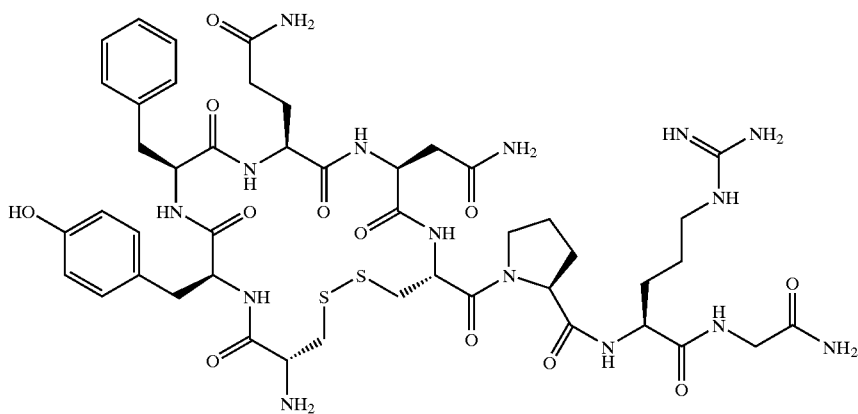

Vasopressi

In fact, such an agent is already in use in human therapy. Desmopressin (otherwise [1-desamino, D-Arg$^8$]vasopressin,

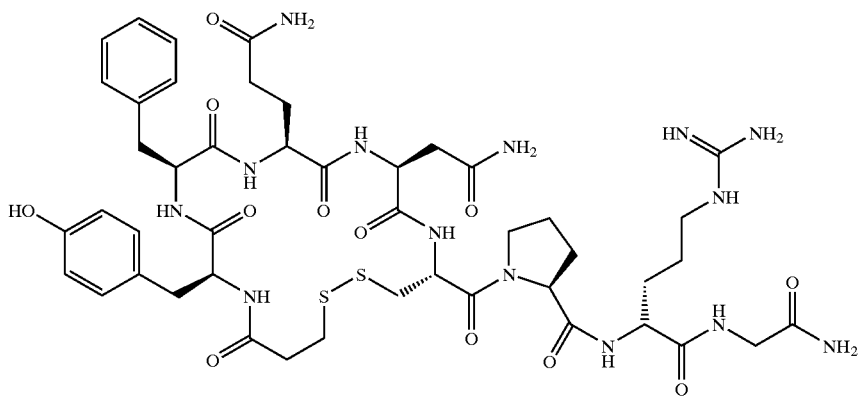

Desmopressin

Overall then, there exists a need for a selective vasopressin V$_2$ receptor agonist that is easy to prepare and purify, and that has a high and predictable oral bioavailability. Such properties are most likely to be obtained with a non-peptide compound. These considerations have led other groups to investigate non-peptide vasopressin V$_2$ agonists, and their results are disclosed in, for example, International Patent Applications WO97/22591, WO99/06403, WO99/06409, WO00/46224, WO00/46225, WO00/46227 and WO00/46228. The compounds disclosed in these documents are, however, less than ideal. In particular, they have poor oral bioavailability, probably due in part to their low aqueous solubility. The present invention provides compounds with improved solubility and bioavailability.

Besides its antidiuretic actions, desmopressin is used to increase the concentration in the blood of the coagulation proteins known as Factor VIII and von Willebrand factor. In the clinical context, this makes desmopressin useful in the treatment of haemophilia A and von Willebrand's disease. Similar applications would be open to the non-peptide agonists of the present invention.

SUMMARY OF THE INVENTION

As disclosed herein, the present invention relates to a series of compounds that are non-peptide agonists of vasopressin and which are selective for the V$_2$ receptor subtype. The compounds are described by general formula 1

1

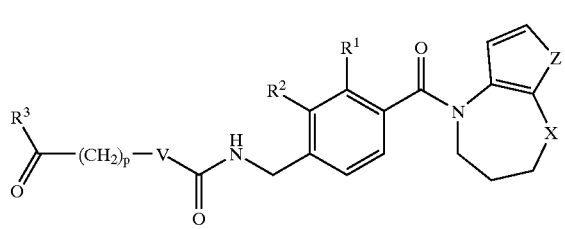

wherein:

V is a covalent bond or NH,

X is selected from CH$_2$, O and N-alkyl,

Z is either S or —CH=CH—,

R$^1$ and R$^2$ are independently selected from H, F, Cl, Br and alkyl,

R$^3$ is selected from OH, O-alkyl and NR$^4$R$^5$,

R$^4$ and R$^5$ are each independently H or alkyl, or together are —(CH$_2$)$_q$—, p is 0, 1, 2, 3 or 4, and q is 4 or 5.

The invention further comprises pharmaceutical compositions incorporating these vasopressin agonists, which compositions are particularly useful in the treatment of central diabetes insipidus, nocturnal enuresis and nocturia.

DESCRIPTION OF THE INVENTION

The present invention comprises N-acyl tetrahydroazepine derivatives defined by general formula 1.

1

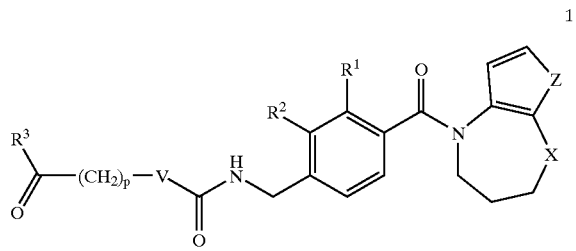

In this formula, V represents an NH group or a covalent bond. X represents a methylene group (—CH$_2$—), an oxygen atom (O) or N-alkyl. Z represents a sulphur atom (S) or a group —CH=CH—.

R$^1$ and R$^2$ are each independently selected from H, F, Cl, Br and alkyl groups.

R$^3$ is selected from OH, O-alkyl and NR$^4$R$^5$.

R$^4$ and R$^5$ are each independently selected from H and alkyl groups. Alternatively, they may together be —(CH$_2$)$_q$—, where q is 4 or 5, such that together with the nitrogen atom to which they are attached they form a pyrrolidine or piperidine ring.

The integer p may take the values 0, 1, 2, 3 and 4. When p is 0, a covalent bond exists between V and the COR$^3$ group. When p is 0 and V is a covalent bond then a single covalent bond exists between the two carbonyl groups.

As used herein, "alkyl" includes saturated hydrocarbon residues, linear or branched, with up to six carbon atoms, such as methyl, ethyl, propyl, isopropyl, n-butyl, sec-butyl, isobutyl, tert-butyl, neopentyl and n-hexyl.

Certain compounds of general formula 1 are capable of forming salts with acids or bases. For example, compounds containing a basic nitrogen atom can form addition salts with mineral and organic acids such as hydrochloric acid, sulphuric acid, phosphoric acid, acetic acid, trifluoroacetic acid, methanesulphonic acid, citric acid and benzoic acid. Compounds containing acidic groups can form salts with bases. Examples of such salts include the sodium, potassium, calcium, triethylammonium and tetraethylammonium salts. Furthermore, compounds that have both acidic and basic groups can form internal salts (zwitterions). Insofar as these salts are pharmaceutically acceptable, they are included within the scope of the invention.

In a preferred embodiment of the invention, the group Z is —CH=CH—.

In another preferred embodiment of the invention, Z is S.

In another preferred embodiment of the invention, X is a methylene group $CH_2$.

In another preferred embodiment of the invention, $R^1$ is a hydrogen atom and $R^2$ is a methyl group or a chlorine atom.

In another preferred embodiment of the invention, $R^1$ is a methyl group or a chlorine atom and $R^2$ is a hydrogen atom.

In another preferred embodiment of the invention, $R^3$ is O-alkyl.

Particularly preferred compounds within the invention combine the features of these preferred embodiments.

Individual preferred compounds within the invention include (but are not limited to) the following:

1-(4-[N-(4-methoxy-4-oxobutanoyl)aminomethyl]-3-methylbenzoyl)-2,3,4,5-tetrahydro-1H-1-benzazepine, 1-(4-[N-(2-methoxy-2-oxoethanoyl)aminomethyl]-3-methylbenzoyl)-2,3,4,5-tetrahydro-1H-1-benzazepine, 1-(4-[N-(2-hydroxy-2-oxoethanoyl)aminomethyl]-3-methylbenzoyl)-2,3,4,5-tetrahydro-1H-1-benzazepine, 1-(4-[N-(5-methoxy-5-oxopentanoyl)aminomethyl]-3-methylbenzoyl)-2,3,4,5-tetrahydro-1H-1-benzazepine, 1-(4-[N-(2-ethoxy-2-oxoethylcarbamoyl)aminomethyl]-3-methylbenzoyl)-2,3,4,5-tetrahydro-1H-1-benzazepine, 1-(4-[N-(2-hydroxy-2-oxoethylcarbamoyl)aminomethyl]-3-methylbenzoyl)-2,3,4,5-tetrahydro-1H-1-benzazepine, 1-(3-methyl-4-[N-(2-methylamino-2-oxoethylcarbamoyl)aminomethyl]benzoyl)-2,3,4,5-tetrahydro-1H-1-benzazepine, 1-(4-[N-(2-dimethylamino-2-oxoethylcarbamoyl)aminomethyl]-3-methylbenzoyl)-2,3,4,5-tetrahydro-1H-1-benzazepine, 1-(4-[N-(2-methoxy-2-oxoethylcarbamoyl)aminomethyl]-3-methylbenzoyl)-2,3,4,5-tetrahydro-1H-1-benzazepine, 1-(4-[N-(2-amino-2-oxoethylcarbamoyl)aminomethyl]-3-methylbenzoyl)-2,3,4,5-tetrahydro-1H-1-benzazepine, 4-(3-chloro-4-[N-(4-methoxy-4-oxobutanoyl)aminomethyl]benzoyl)-5,6,7,8-tetrahydro-4H-thieno[3,2-b]azepine, 5-(4-[N-(4-methoxy-4-oxobutanoyl)aminomethyl]benzoyl)-2,3,4,5-tetrahydro-1,5-benzoxazepine, 1-(4-[N-(2-ethoxy-2-oxoethylcarbamoyl)aminomethyl]-3-methylbenzoyl)-5-methyl-2,3,4,5-tetrahydro-1H-1,5-benzodiazepine, 1-(4-[N-(3-methoxy-3-oxopropanoyl)aminomethyl]-3-methylbenzoyl)-2,3,4,5-tetrahydro-1H-1-benzazepine, 1-(4-[N-(3-ethoxy-3-oxopropanoyl)aminomethyl]-3-methylbenzoyl)-2,3,4,5-tetrahydro-1H-1-benzazepine, 1-(4-[N-(3-hydroxy-3-oxopropanoyl)aminomethyl]-3-methylbenzoyl)-2,3,4,5-tetrahydro-1H-1-benzazepine, 1-(4-[N-(4-hydroxy-4-oxobutanoyl)aminomethyl]-3-methylbenzoyl)-2,3,4,5-tetrahydro-1H-1-benzazepine, 1-(4-[N-(5-hydroxy-5-oxopentanoyl)aminomethyl]-3-methylbenzoyl)-2,3,4,5-tetrahydro-1H-1-benzazepine, 1-(4-[N-(3-methoxy-3-oxopropanoyl)aminomethyl]-2-methylbenzoyl)-2,3,4,5-tetrahydro-1H-1-benzazepine, 1-(4-[N-(N-'-ethoxycarbonylcarbamoyl)aminomethyl]-3-methylbenzoyl)-2,3,4,5-tetrahydro-1H-1-benzazepine, 1-(4-[N-(2-ethoxy-2-oxoethylcarbamoyl)aminomethyl]-2-methylbenzoyl)-2,3,4,5-tetrahydro-1H-1-benzazepine, 1-(4-[N-(2-isopropoxy-2-oxoethylcarbamoyl)aminomethyl]-3-methylbenzoyl)-2,3,4,5-tetrahydro-1H-1-benzazepine, 1-(4-[N-(2-tert-butoxy-2-oxoethylcarbamoyl)aminomethyl]-3-methylbenzoyl)-2,3,4,5-tetrahydro-1H-1-benzazepine, 1-(3-chloro-4-[N-(2-dimethylamino-2-oxoethylcarbamoyl)aminomethyl]benzoyl)-2,3,4,5-tetrahydro-1H-1-benzazepine, 1-(3-methyl-4-[N-(2-(1-piperidino)-2-oxoethylcarbamoyl)aminomethyl]benzoyl)-2,3,4,5-tetrahydro-1H-1-benzazepine, 1-(3-methyl-4-[N-(2-(1-pyrrolidino)-2-oxoethylcarbamoyl)aminomethyl]benzoyl)-2,3,4,5-tetrahydro-1H-1-benzazepine, 1-(4-[N-(3-ethoxy-3-oxopropylcarbamoyl)aminomethyl]-3-methylbenzoyl)-2,3,4,5-tetrahydro-1H-1-benzazepine, and 1-(4-[N-(3-hydroxy-3-oxopropylcarbamoyl)aminomethyl]-3-methylbenzoyl)-2,3,4,5-tetrahydro-1H-1-benzazepine The compounds of the present invention can be prepared using methods generally known in the art. The compounds of general formula 1 can be considered to be composed of three linked fragments (A–C).

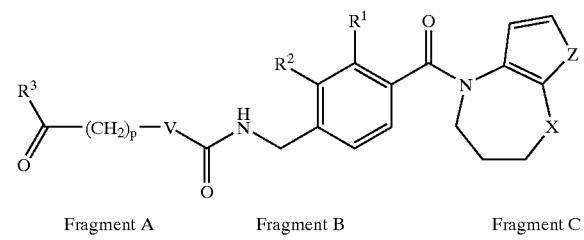

Fragment A     Fragment B     Fragment C

The three fragments will generally be prepared separately and then combined at a late stage in the synthesis. Some instances of the various groups (particularly $R^3$ and X) might be incompatible with this assembly and so will require the use of protecting groups. The use of protecting groups is well known in the art (see for example "Protective Groups in Organic Synthesis", T. W. Greene, Wiley-Interscience, 1981). Particular groups that may require protection are amines (protected as amides or carbamates) and carboxylic acids (protected as esters). For the purposes of this discussion, it will be assumed that such protecting groups as are necessary are in place.

The fragments A, B and C can be combined according to two strategies to give the compounds of formula 1. In the first, fragments A and B are linked to give a fragment corresponding to AB, which is then combined with fragment C. In the second, fragments B and C are linked to give a fragment corresponding to BC, which is then combined with fragment A. The chemistry involved in the condensation of fragment A with B, and that involved in the condensation of fragment B with fragment C, will be the same whichever strategy is followed.

Formation of Fragment AB

The nature of the A—B bond forming reaction depends on the identity of V.

V = covalent bond

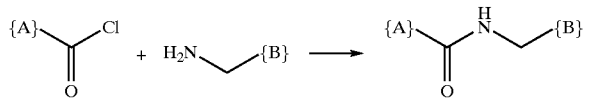

Here, {A} and {B} represent part structures of the fragments A and B respectively. The formation of amides by the reaction of acid chlorides with primary amines is well known. In general, the amine and the acid chloride are mixed in an aprotic solvent such as dichloromethane or dimethylformamide in the presence of a tertiary amine such as triethylamine.

V = NH

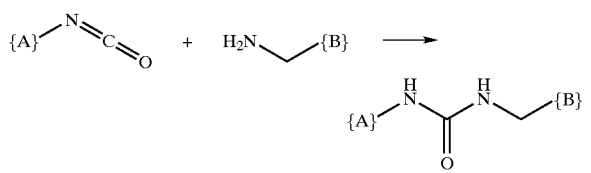

The formation of ureas by the reaction between an isocyanate and a primary amine is also well known. In general, the amine and the isocyanate are mixed in an aprotic solvent such as dichloromethane or dimethylformamide. The presence of a tertiary amine such as triethylamine may be beneficial, but is generally not necessary.

Fromation of fragment BC

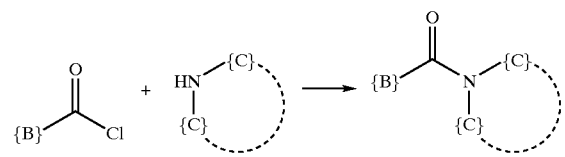

Formation of the amide bond between fragments B and C can be most easily achieved by allowing the acid chloride corresponding to fragment B to react with the secondary amine that is part of the azepine ring of fragment C. The reaction proceeds in an aprotic solvent in the presence of a tertiary amine base. Depending on the exact nature of the two fragments, this reaction may require more or less time to achieve satisfactory yields of the product. Alternatively, the carboxylic acid corresponding to fragment B may be condensed with the azepine using one of the many reagents known in the art to effect such amide bond forming reactions.

Overall then, the following intermediates are required for the synthesis of the compounds of the present invention.

i) For Fragment A

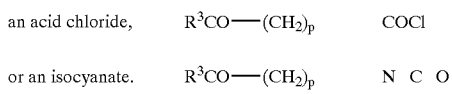

an acid chloride, $R^3CO$—$(CH_2)_p$ $COCl$ or an isocyanate. $R^3CO$—$(CH_2)_p$ $NCO$ Acid chlorides are well known. Many are items of commerce or described in the literature. Where the necessary acid chloride is not a known compound, it will generally be available in a single step from the corresponding carboxylic acid. Isocyanates are also well known. In general, they can be prepared from the corresponding primary amine by reaction with phosgene or an equivalent reagent.

ii) For Fragment B

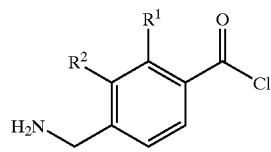

Because the primary amine and acid chloride groups are incompatible, they must be developed separately and protected. The acid chloride can be elaborated from the corresponding carboxylic acid, which is conveniently protected as its methyl ester. The primary amine can be elaborated from the corresponding nitrile (by reduction) or the alcohol (by displacement with a nitrogen nucleophile). The best method will depend on the nature of the substituents $R^1$ and $R^2$.

iii) For Fragment C

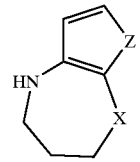

Fused azepines of this type are prepared according to the methods described in the literature.

The present invention further comprises pharmaceutical compositions that include at least one compound according to the foregoing description as an active constituent. The composition may also include a second pharmacological agent such as a spasmolytic or a potassium channel blocker, these agents being known in the art to ameliorate bladder dysfunction. Preferably, the composition includes only one active constituent. The composition will include excipients selected from binding agents, bulking agents, dispersants, solvents, stabilising agents and the like, such excipients being generally known in the art.

The excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation will be a tablet or capsule. Other formulations include dry powders, solutions, suspensions, suppositories and the like.

In a further aspect, the present invention is a method of treating or controlling certain human physiological dysfunctions. This method comprises the administration to the person in need of such treatment of an effective amount of a pharmaceutical composition, which composition contains a compound according to the foregoing description as an active constituent. The compounds act to reduce urine output, and so the method of the invention can be applied to all conditions in which elevated urine output is a contributory factor. The compounds also increase the production of the blood coagulation proteins known as Factor VIII and von Willebrand factor, and so the treatment of bleeding disorders can be undertaken.

In a preferred embodiment, the condition treated is diabetes insipidus. This is a condition caused by an inability of the body to produce and secrete physiologically active vasopressin, with the result that water re-uptake is greatly reduced and large volumes of urine are produced.

In another preferred embodiment, the condition treated is nocturnal enuresis. This is defined as bladder emptying while the individual is sleeping. It is a condition that mainly affects children and a number of factors may be involved in its etiology.

In another preferred embodiment, the condition treated is nocturia. This is defined as production of sufficient urine during the night to require the individual to wake and empty his (or her) bladder. Again, this condition may be the result of a number of factors.

In another preferred embodiment, the condition treated is incontinence. This condition is characterised, in part, by reduced bladder capacity and control such that involuntary urination occurs unless the bladder is emptied frequently. Incontinence has been divided into two conditions, stress incontinence and urge incontinence. A number of etiological factors are thought to be involved. Treatment according to the invention is particularly useful for delaying the need for bladder emptying ("voiding postponement") in order to allow the incontinent subject a dry period of a few hours (such as up to four hours). Such voiding postponement may also be useful for the non-continent population, for example for people obliged to remain in meetings for extended periods.

In another preferred embodiment, the condition treated is haemophilia A or von Willebrand's disease. These are conditions in which Factor VIII or von Willebrand factor production is reduced and the individual suffers from prolonged bleeding.

In another preferred embodiment, the composition is administered prior to surgery (including dental surgery) to increase the coagulability of the blood and so reduce perioperative blood loss.

The administration of the compositions of the present invention will generally be under the control of a physician. The physician will determine the amount of composition to be administered and the dosing schedule, taking into account the patient's physical condition and the therapeutic goals. For an adult diabetes insipidus patient, a typical dose might be between 50 mg and 1 g of the active compound per day, taken as a single tablet or as up to four tablets throughout the day. For routes of administration other than the oral route, the amount of compound will be reduced, since non-oral routes tend to be more efficient in terms of delivering therapeutic agents into the systemic circulation. For the treatment of haemophilia A and von Willebrand's disease the amount of compound may need to be higher than for the treatment of diabetes insipidus.

The foregoing general description will now be further illustrated with a number of non-limiting examples.

EXAMPLES

Abbreviations

The following abbreviations have been used.

| | |
|---|---|
| AIBN | Azo-bis-(isobutyronitrile) |
| BOC | tert-Butyloxycarbonyl |
| (BOC)$_2$O | Di-tert-butyl dicarbonate |
| DIEA | Diisopropylethylamine |
| DMF | Dimethylformamide |
| EtOAc | Ethyl acetate |
| IPA | Isopropanol |
| M.S. | Mass spectrometry |
| NBS | N-Bromosuccinimide |
| NMR | Nuclear magnetic resonance spectrometry |
| pet. ether | petroleum ether, fraction boiling at 60–80° C. |
| PyBroP ® | Bromotris(pyrrolidino)phophonium hexafluorophosphate |
| THF | Tetrahydrofuran |
| WSCDI | Water-soluble carbodiimide |

Preparation of Intermediates

Reagents corresponding to fragment A and C were commercially available or prepared according to the published procedures except where detailed in the specific Examples.

Reagents corresponding to fragment B were prepared as detailed below.

Example A 4-(tert-Butyloxycarbonylaminomethyl)-3-chlorobenzoic Acid

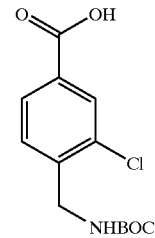

A1. Methyl 4-Bromomethyl-3-chlorobenzoate

To a solution of methyl 3-chloro-4-methylbenzoate (5.0 g, 27.1 mmol) in carbon tetrachloride (50 ml) were added NBS (5.8 g, 32.0 mmol) and AIBN (0.442 g, 2.70 mmol). The mixture was stirred at reflux for 18 h. The mixture was allowed to cool to room temperature and then concentrated in vacuo. The residue was purified by flash chromatography on silica (eluant EtOAc:pet. ether 0:100 to 5:95); yield 5.96 g (84%).

A2. 4-(tert-Butyloxycarbonylaminomethyl)-3-chlorobenzoic Acid

To a saturated solution of ammonia in ethanol (170 ml) was added methyl 4-bromomethyl-3-chlorobenzoate from Example A1 (5.5 g, 20.9 mmol). The mixture was stirred at room temperature for 1 h and then concentrated in vacuo. The residue was triturated with diethyl ether and the resultant white crystals were filtered off and washed with more diethyl ether. To a solution of this solid in water (100 ml) were added solutions of (BOC)$_2$O (5.0 g, 23.0 mmol) in dioxan (100 ml) and sodium hydroxide (1.86 g, 46.0 mmol) in water (100 ml). The mixture was stirred at room temperature for 18 h and then concentrated in vacuo. The aqueous residue was acidified with citric acid and extracted with chloroform/IPA. The organic layer was washed with water, dried over MgSO$_4$, and concentrated in vacuo to give a white solid; yield 2.8 g (67%).

Example B

4-Cyano-3-methylbenzoic Acid

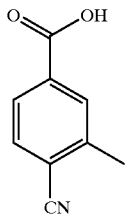

To a solution of 4-bromo-2-methylbenzonitrile (2.0 g, 10.2 mmol) in THF (100 ml) at −78° C. under a nitrogen atmosphere was added dropwise a 2.5M solution of n-butyl lithium (4.48 ml, 11.2 mmol). The mixture was stirred at −78° C. for 1 h and then poured onto solid carbon dioxide (5 g) in THF (50 ml). The mixture was allowed to warm to room temperature. Water was added (200 ml) and the mixture was extracted with diethyl ether (3 times). The aqueous layer was acidified by addition of concentrated HCl and extracted with chloroform (3 times). The combined chloroform extracts were washed with water, dried over MgSO$_4$, and concentrated in vacuo to give a white solid; yield 1.2 g (73%).

Example C

4-Cyano-2-methylbenzoic Acid

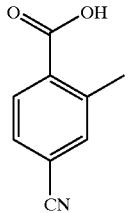

4-Bromo-3-methylbenzonitrile (2.0 g, 10.2 mmol) was reacted following the method of Example B to give a yellow solid which was triturated with hexane and filtered off; yield 0.96 g (59%).

Example D 4-(tert-Butyloxycarbonylaminomethyl)-2-fluorobenzoic Acid

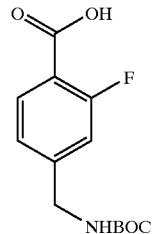

D1. 2-Fluoro-4-methylbenzoic Acid

4-Bromo-3-fluorotoluene (8.33 g, 44.07 mmol) was reacted following the method of Example B to give a white solid; 4.89 g (72%).

D2. Methyl 2-Fluoro-4-methylbenzoate

To a solution of 2-fluoro-4-methylbenzoic acid from Example D1 (6.04 g, 39.18 mmol) in toluene (80 ml) was added thionyl chloride (6.5 ml, 89.11 mmol). The mixture was heated at reflux for 2.5 h, cooled and concentrated in vacuo. The residue was dissolved in dichloromethane (50 ml) and methanol (50 ml) was added. The mixture was stirred at room temperature for 2.5 h and then concentrated in vacuo. The residue was dissolved in dichloromethane (100 ml), washed with saturated sodium bicarbonate solution and brine, dried over MgSO$_4$, and concentrated in vacuo to give a tan solid; yield 5.07 g (77%).

D3. Methyl 4-Bromomethyl-2-fluorobenzoate

Methyl 2-fluoro-4-methylbenzoate from Example D2 (5.07 g, 30.16 mmol) was reacted following the method of Example of A1. The product was purified by flash chromatography on silica (eluant EtOAc:pet. ether 20:80); yield 5.9 g (80%).

D4. 4-(tert-Butyloxycarbonylaminomethyl)-2-fluorobenzoic Acid

Methyl 4-bromomethyl-2-fluorobenzoate from Example D3 (5.9 g, 24.13 mmol) was reacted following the method of Example A2. The product was recrystallised from dioxan/pet. ether to give white crystals; yield 2.46 g (38%).

Reagents corresponding to fragments A, B and C were combined to give the specific Examples as detailed below.

Example 1

1-(4-[N-4-Methoxy-4-oxobutanoyl)aminomethyl]-3-methylbenzoyl)-2,3,4,5-tetrahydro-1H-1-benzazepine

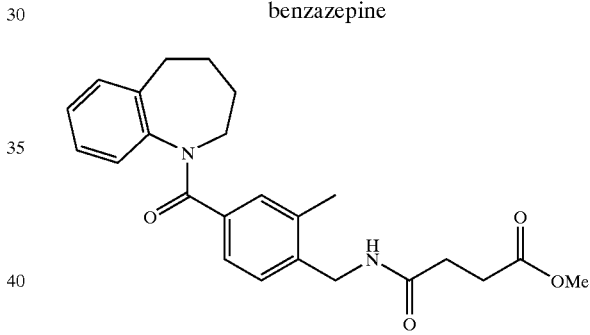

1A. 1-(4-Cyano-3-methylbenzoyl)-2,3,4,5-tetrahydro-1H-1-benzazepine

To a solution of 2,3,4,5-tetrahydro-1H-1-benzazepine (0.80 g, 5.44 mmol) in dichloromethane (40 ml) were added 4-cyano-3-methylbenzoic acid from example B (0.96 g, 5.95 mmol), triethylamine (0.76 g, 5.44 mmol), 4-(dimethylamino)pyridine (0.66 g, 5.44 mmol) and WSCDI (2.17 g, 10.88 mmol). The mixture was stirred at reflux for 18 h, cooled and evaporated in vacuo. The residue was partitioned between EtOAc and 1M KHSO$_4$. The organic layer was washed with saturated sodium bicarbonate solution and brine, dried over MgSO$_4$, and concentrated in vacuo. The residue was purified by flash chromatography on silica (eluant EtOAc:pet. ether 30:70); yield 1.10 g (70%).

1B. 1-(4-[Aminomethyl]-3-methylbenzoyl)-2,3,4,5-tetrahydro-1H-1-benzazepine Hydrochloride To a degassed solution of the cyanobenzoyl benzazepine from Example 1A (1.10 g, 3.79 mmol) in methanol (40 ml) were added concentrated hydrochloric acid (0.98 ml, 11.3 mmol) and 10% palladium-on-carbon (0.80 g). Hydrogen gas was bubbled through the mixture for 5 h at room temperature. The catalyst was removed by filtration through a pad of celite and the filtrate was evaporated in vacuo to give the product as the HCl salt; yield 1.23 g (98%).

1C. 1-(4-[N-(4-Methoxy-4-oxobutanoyl)aminomethyl]-3-methylbenzoyl)-2,3,4,5-tetrahydro-1H-1-benzazepine To a solution of the amine from Example 1B (0.10 g, 0.30 mmol) in dichloromethane (10 ml) were added triethylamine (0.061 ml, 0.90 mmol) and 3-carbomethoxy propionyl chloride (0.046 g, 0.30 mmol). The mixture was stirred at room temperature for 18 h and then washed with 1M KHSO$_4$ (3 times), water and brine, dried over Na$_2$SO$_4$, and concentrated in vacuo to give a white solid; yield 0.10 g (81%).

$^1$H NMR: δ 1.40–1.60 (1H, m), 1.84–2.20 (3H, m), 2.15 (3H, s), 2.40–2.54 (2H, m), 2.58–2.92 (4H, m), 2.94–3.10 (1H, m), 3.65 (3H, s), 4.30 (2H, d, J=5.6 Hz), 4.99 (1H, d, J=12.9 Hz), 5.90 (1H, s), 6.62 (1H, d, J=7.9 Hz), 6.78–6.96 (3H, m), 7.00–7.16 (2H, m), 7.21 (1H, m) ppm. M.S.: calc m/e=408; found [M+H]$^+$=409.

Example 2

1-4-[N-(2-Methoxy-2-oxoethanoyl)aminomethyl]-3-methylbenzoyl)-2,3,4,5-tetrahydro-1H-1-benzazepine

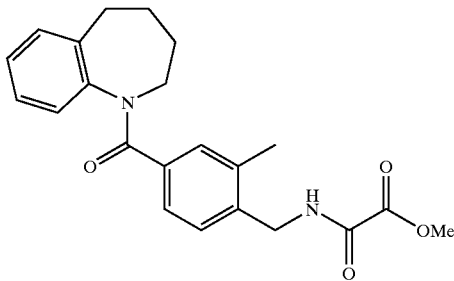

The amine hydrochloride from Example 1B (0.10 g, 0.30 mmol) was reacted with methyl oxalyl chloride (0.037 g, 0.30 mmol) according to the procedure in Example 1C to give a white solid; yield 0.085 g (76%).

$^1$H NMR: δ 1.48–1.70 (1H, m), 1.96–2.16 (3H, m), 2.26 (3H, s), 2.78–3.18 (3H, m), 3.98 (3H, s), 4.50 (2H, d, J=6.8 Hz), 5.08 (1H, d, J=12.7 Hz), 6.72 (1H, d, 7.6 Hz), 6.88–7.06 (3H, m), 7.18 (1H, t, J=7.6 Hz), 7.22–7.36 (2H, m) ppm. M.S.: calc m/e=380; found [M+H]$^+$=381.

Example 3

1-(4-[N-2-Hydroxy-2-oxoethanoyl)aminomethyl]-3-methylbenzoyl)-2,3,4,5-tetrahydro-1H-1-benzazepine

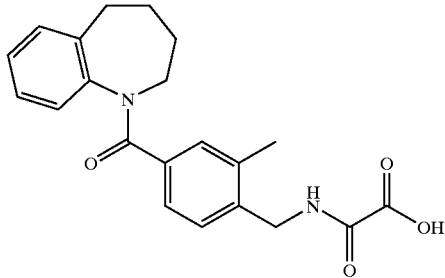

To a solution of the methyl ester from Example 2 (0.045 g, 0.118 mmol) in THF (10 ml) and water (5 ml) was added lithium hydroxide monohydrate (0.010 g, 0.23 mmol). The mixture was stirred at room temperature for 2 h, acidified to pH 1 by addition of 1M HCl and extracted with EtOAc (3 times). The combined organic extracts were washed with brine, dried over Na$_2$SO$_4$, and concentrated in vacuo to give a white solid; yield 0.034 g (76%).

$^1$H NMR: δ 1.40–1.62 (1H, m), 1.84–2.24 (3H, s), 2.17 (3H, s), 2.70–3.10 (3H, m), 4.40 (2H, d, J=5.9 Hz), 4.99 (1H, d, J=12.9 Hz), 6.63 (1H, d, J=7.6 Hz), 6.80–6.98 (3H, m), 7.02–7.28 (3H, m), 7.38 (1H, br s) ppm. M.S.: calc m/e=366; found [M+H]$^+$=367.

Example 4

1-(4-[N-(5-Methoxy-5-oxopentanoyl)aminomethyl]-3-methylbenzoyl)-2,3,4,5-tetrahydro-1H-1-benzazepine

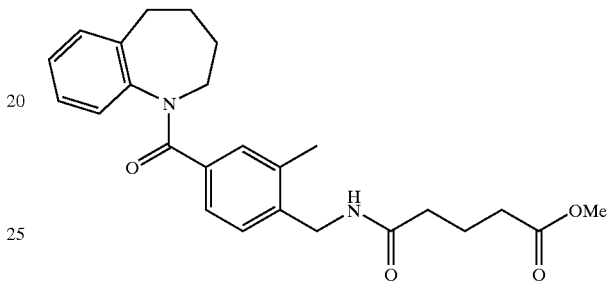

The amine hydrochloride from Example 1B (0.10 g, 0.30 mmol) was reacted with methyl 4-(chloroformyl) butyrate (0.050 g, 0.30 mmol) according to the procedure in Example 1C to give a white solid; yield 0.061 g (48%).

$^1$H NMR: δ 1.42–1.62 (1H, m), 1.84–2.28 (8H, m), 2.30–2.50 (4H, m), 2.70–2.94 (2H, m), 2.96–3.12 (1H, m), 3.65 (3H, s), 4.31 (2H, d, J=5.3 Hz), 4.99 (1H, d, J=13.9 Hz), 5.75 (1H, br s), 6.63 (1H, d, J=7.6 Hz), 6.78–6.98 (3H, m), 7.02–7.16 (2H, m), 7.21 (1H, d, J=6.6 Hz) ppm. M.S.: calc m/e=422; found [M+H]$^+$=423.

Example 5

1-(4-[N-(2-Ethoxy-2-oxoethylcarbamoyl)aminomethyl]-3-methylbenzoyl)-2,3,4,5-tetrahydro-1H-1-benzazepine

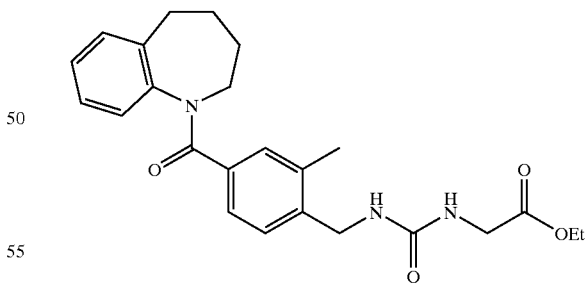

To a solution of the amine from Example 1B (0.10 g, 0.30 mmol) in dichloromethane (10 ml) were added triethylamine (0.061 ml, 0.90 mmol) and ethyl isocyanatoacetate (0.059 g, 0.45 mmol). The mixture was stirred at room temperature for 18 h and then washed with 1M KHSO$_4$ (3 times), water and brine, dried over Na$_2$SO$_4$, and concentrated in vacuo to give a white solid; yield 0.10 g (81%).

$^1$H NMR: δ 1.18 (3H, t, J=7.3 Hz), 1.38–1.55 (1H, m), 1.80–2.10 (3H, m), 1.95 (3H, s), 2.60–2.98 (3H, m), 3.84

(2H, s), 4.04 (2H, s), 4.07 (2H, q, J=7.3 Hz), 4.87–4.92 (1H, m), 5.73 (2H, br s), 6.50 (1H, d, J=7.3 Hz), 6.63–6.97 (5H, m), 7.11 (1H, d, J=7.3 Hz) ppm. M.S.: calc m/e=423; found [M+H]$^+$=424.

Example 6

1-(4-[N-(Carboxymethylcarbamoyl)aminomethyl]-3-methylbenzoyl)-2,3,4,5-tetrahydro-1H-1-benzazepine

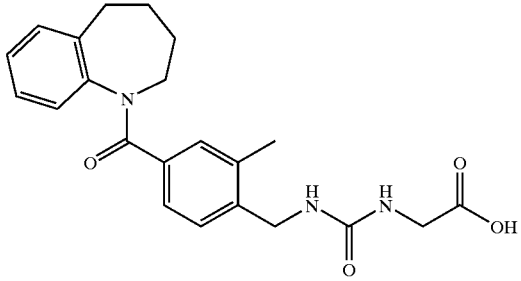

To a solution of the ethyl ester from Example 5 (0.050 g, 0.10 mmol) in THF (20 ml) and water (5 ml) was added lithium hydroxide monohydrate (0.020 g, 0.45 mmol). The mixture was stirred at room temperature for 4 h. The mixture was concentrated in vacuo and the residue diluted with water then washed with diethyl ether. The aqueous layer was acidified to pH 1 by addition of 1M HCl and extracted with EtOAc (3 times). The combined organic extracts were washed with brine, dried over Na$_2$SO$_4$, and concentrated in vacuo to give a white solid; yield 0.046 g (99%).

$^1$H NMR: δ 1.30–1.50 (1H, m), 1.75–2.05 (3H, m), 1.94 (3H, s), 2.60–2.98 (3H, m), 3.59 (2H, br s), 4.01 (2H, br s), 4.80–4.85 (1H, m), 6.05 (2H, br s), 6.53 (1H, d, J=7.2 Hz), 6.75–6.99 (5H, m), 7.11 (1H, d, J=7.2 Hz) ppm. M.S.: calc m/e=395; found [M+H]$^+$=396.

Example 7

1-(4-[N-(2-Methylamino-2-oxoethylcarbamoyl)aminomethyl]-3-methylbenzoyl)-2,3,4,5-tetrahydro-1H-1-benzazepine

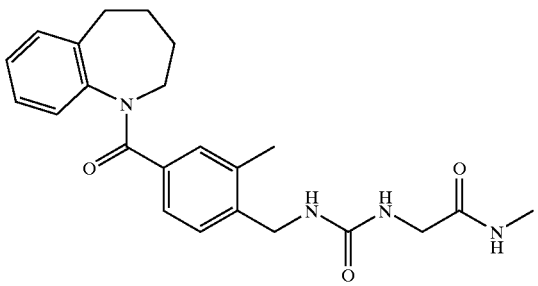

To a solution of the carboxylic acid from Example 6 (0.109, 0.25 mmol) in dichloromethane (25 ml) was added DIEA (0.221 ml, 1.26 mmol) and PyBroP (0.129 g, 0.278 mmol). The mixture was stirred at room temperature for 10 min and then methylamine hydrochloride (0.085 g, 1.26 mmol) was added. Stirring was continued for a further 3 h. The mixture was then washed with 1M KHSO$_4$ (3 times), saturated sodium bicarbonate solution (3 times) and brine, dried over Na$_2$SO$_4$, and concentrated in vacuo. The residue was purified by flash chromatography on silica (eluant dichloromethane:methanol 96:4) to give a white solid; yield 0.018 g (17%).

$^1$H NMR: δ 1.40–1.60 (1H, m), 1.80–2.00 (2H, m), 2.00–2.20 (3H, s), 2.60 (3H, d, J=4.0 Hz), 2.65–3.05 (3H, m), 3.60 (2H, d, J=4.0 Hz), 4.15 (2H, d, J=4.0 Hz), 4.90–5.00 (1H, m), 6.10–6.30 (2H, m), 6.60 (1H, d, J=8.0 Hz), 6.70–7.20 (8H, m) ppm. M.S.: calc m/e=408; found [M+H]$^+$=409.

Example 8

1-(4-[N-(2-Dimethylamino-2-oxoethylcarbamoyl)aminomethyl]-3-methylbenzoyl)-2,3,4,5-tetrahydro-1H-1-benzazepine

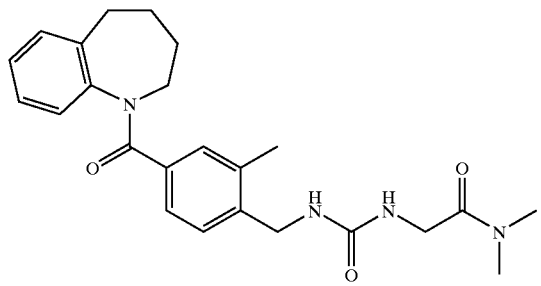

The carboxylic acid from Example 6 (0.07 g, 0.18 mmol) was reacted with dimethylamine hydrochloride (0.072 g, 0.88 mmol) according to the procedure in Example 7. The product was purified by flash chromatography on silica (eluant chloroform:methanol:acetic acid 98:1:1) to give a white solid; yield 0.08 g (11%).

$^1$H NMR: δ 1.39–1.50 (1H, m), 1.86–2.10 (3H, m), 2.07 (3H, s), 2.57 (3H, s), 2.60–3.00 (3H, m), 2.85 (3H, s), 3.95 (2H, d, J=4.0 Hz), 4.16 (2H, d, J=5.6 Hz), 4.90–5.00 (1H, m), 5.74 (1H, br s), 6.11 (1H, br s), 6.54 (1H, d, J=7.6 Hz), 6.78–7.18 (6H, m) ppm. M.S.: calc m/e=422; found [M+H]$^+$=423.

Example 9

1-(4-[N-(2-Methoxy-2-oxoethylcarbamoyl)aminomethyl]-3-methylbenzoyl)-2,3,4,5-tetrahydro-1H-1-benzazepine

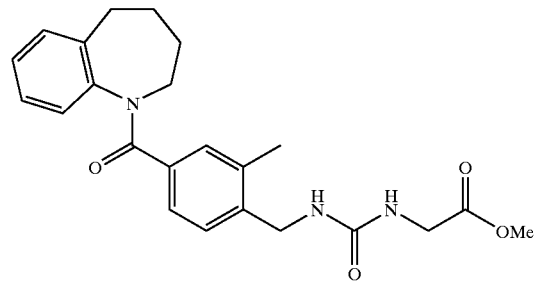

To a solution of the carboxylic acid from Example 6 (0.080 g, 0.20 mmol) under a nitrogen atmosphere in dichloromethane (25 ml) at 0° C. were added DMF (20 μl) and oxalyl chloride (31 mg, 0.24 mmol). The mixture was stirred at 0° C. to room temperature for 2 h and then concentrated in vacuo. The residue was dissolved in methanol (4 ml) and dichloromethane (16 ml) and the mixture stirred at room temperature for 16 h. The mixture was then washed with 1M KHSO$_4$ (3 times), saturated sodium bicarbonate solution (3 times) and brine, dried over Na$_2$SO$_4$, and concentrated in vacuo. The residue was purified by flash chromatography on silica (eluant dichloromethane:methanol 96:4) to give a white solid; yield 0.049 g (60%).

$^1$H NMR: δ 1.38–1.50 (1H, m), 1.80–2.00 (3H, m), 2.00 (3H, s), 2.60–3.00 (3H, m), 3.64 (3H, s), 3.90 (2H, s), 4.10 (2H, s), 4.85–4.95 (1H, m), 6.52 (1H, d, J=7.2 Hz), 6.67–7.02 (7H, m), 7.13 (1H, d, J=6.2 Hz) ppm. M.S.: calc m/e=409; found [M+H]$^+$=410.

Example 10

1-(4-[N-(2-Amino-2-oxoethylcarbamoyl)aminomethyl]-3-methylbenzoyl)-2,3,4,5-tetrahydro-1H-1-benzazepine

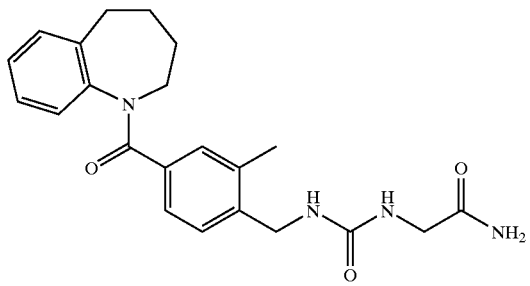

To a solution of the carboxylic acid from Example 6 (0.10 g, 0.25 mmol) in dichloromethane (20 ml) were added hydroxybenzotriazole (34 mg, 0.25 mmol) and WSCDI (51 mg, 0.25 mmol). The mixture was stirred at room temperature for 10 min. Ammonia 880 (0.5 ml) was then added and stirring continued for a further 16 h. The mixture was concentrated in vacuo and the residue purified by flash chromatography on silica (eluant ethyl acetate) to give a white solid; yield 0.008 g (8%).

$^1$H NMR: δ 1.40–1.76 (2H, m), 1.84–2.16 (2H, m), 2.29 (3H, s), 2.66–3.10 (3H, s), 3.95 (2H, s), 4.56 (2H, s), 4.99 (1H, d, J=13.9 Hz), 5.59 (1H, br s), 6.63 (1H, d, J=7.9 Hz), 6.80–6.98 (3H, m), 7.00–7.12 (2H, m), 7.20 (1H, d, J=7.3 Hz) ppm. M.S.: calc m/e=394; found [M+H]$^{+-}$395.

Example 11

4-(4-[N-(4-Methoxy-4-oxobutanoyl)aminomethyl]-3-chlorobenzoyl)-5,6,7,8-tetrahydro-4H-thieno[3,2-b]azepine

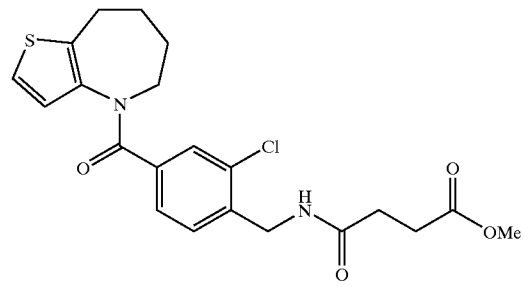

11A. 4-(4-[N-(tert-Butyloxycarbonyl)aminomethyl]-3-chlorobenzoyl)-5,6,7,8-tetrahydro-4H-thieno[3.2-b]azepine Hydrochloride The carboxylic acid from A2 (0.60 g, 2.10 mmol) was reacted with 5,6,7,8-tetrahydro-4H-thieno[3,2-b]azepine (0.28 g, 1.80 mmol) according to the procedure in example 1A. The product was purified by flash chromatography on silica (eluant EtOAc:pet. ether 40:60) to give a yellow solid.

11B. 4-(4-[Aminomethyl]-3-chlorobenzoyl)-5,6,7,8-tetrahydro-4H-thieno[3,2-b]azepine Hydrochloride The BOC amine from 11A was dissolved in 4N HCl/dioxan (30 ml). The mixture was stirred at room temperature for 40 min then concentrated in vacuo to leave a tan solid; yield 0.41 g (63%, for 2 steps).

11C. 4-(4-[N-(4-Methoxyyoxobutanoyl)aminomethyl]-3-chlorobenzoyl)-5,6,7,8-tetrahydro-4H-thieno[3,2-b]azerine To a solution of the amine from Example 11B (0.0329, 0.08 mmol) in dichloromethane (10 ml) were added triethylamine (0.025 ml, 0.18 mmol) and 3-carbomethoxypropionyl chloride (0.014 g, 0.08 mmol). The mixture was stirred at room temperature for 18 h and then washed with 1M KHSO$_4$ (3 times), water and brine, dried over Na$_2$SO$_4$, and concentrated in vacuo. The residue was purified by flash chromatography on silica (eluant EtOAc:pet. ether 50:50–90:10); yield 0.022 g (56%).

$^1$H NMR: δ 1.70–1.86 (3H, m), 1.96–2.08 (2H, m), 2.44–2.56 (2H, m), 2.60–2.72 (2H, m), 2.86–2.98 (2H, m), 3.67 (3H, s), 3.85 (1H, br s), 4.44 (2H, d, J=5.9 Hz), 6.18 (1H, d, J=5.3 Hz), 6.28 (1H, br s), 6.68 (1H, d, J=5.3 Hz), 7.03 (1H, d, J=7.6 Hz), 7.15 (1H, d, J=7.6 Hz) ppm. M.S.: calc m/e=434; found [M+H]$^+$ $^{35}$Cl=435.

Examples 12–28

The following compounds were prepared by methods analogous to those described above.

| Example | X | p | V | R$^1$ | R$^2$ | R$^3$ | [M + H]$^+$ |
|---|---|---|---|---|---|---|---|
| 12 | O | 2 | — | H | H | OMe | 397 |
| 13 | NMe | 1 | NH | H | Me | OEt | 439 |
| 14 | CH$_2$ | 1 | — | H | Me | OMe | 415 |
| 15 | CH$_2$ | 1 | — | H | Me | OEt | 409 |
| 16 | CH$_2$ | 1 | — | H | Me | OH | 381 |
| 17 | CH$_2$ | 2 | — | H | Me | OH | 395 |
| 18 | CH$_2$ | 3 | — | H | Me | OH | 409 |
| 19 | CH$_2$ | 1 | — | Me | H | OMe | 395 |
| 20 | CH$_2$ | 0 | NH | H | Me | OEt | 410 |
| 21 | CH$_2$ | 1 | NH | Me | H | OEt | 424 |
| 22$^a$ | CH$_2$ | 1 | NH | H | Me | OiPr | 438 |
| 23$^b$ | CH$_2$ | 1 | NH | H | Me | OtBu | 452 |
| 24$^c$ | CH$_2$ | 1 | NH | H | Cl | NMe$_2$ | 443 |
| 25 | CH$_2$ | 1 | NH | H | Me | piperidinyl | 463 |

-continued

| Example | X | p | V | R¹ | R² | R³ | [M + H]⁺ |
|---|---|---|---|---|---|---|---|
| 26 | CH₂ | 1 | NH | H | Me | (pyrrolidinyl) | 449 |
| 27[d] | CH₂ | 2 | NH | H | Me | OEt | 438 |
| 28[e] | CH₂ | 2 | NH | H | Me | OH | 410 |

Selected ¹H NMR data:
a  1.17(6H, d, J=6.3 Hz), 1.20–1.24 (1H, m), 1.80–2.10(3H, m), 2.00 (3H, s), 2.60–3.00 (3H, m), 3.85(2H, d, J=5.3 Hz), 4.10(2H, d, J=4.9 Hz), 4.82–4.85(1H, m), 4.96(1H, sept, J=6.2 Hz), 5.33(1H, t, J=5.2 Hz), 5.43(1H, t, J=4.9 Hz), 6.52(1H, d, J=7.6 Hz) ppm.
b  1.38–1.42(1H, m), 1.38(9H, s), 1.78–2.10(3H, m), 1.97(3H, s), 2.60–3.00(3H, m), 3.78 (2H, s), 4.07(2H, s), 4.89–4.94(1H, m), 5.50 (2H, br s), 6.51(1H, d, J=7.9 Hz), 6.64–6.98(5H, m), 7.12(1H, d, J=7.7 Hz) ppm.
c  1.38–1.50(1H, m), 1.80–2.06(3H, m), 2.60–3.00(3H, m), 2.70(3H, s), 2.87(3H, s), 3.96(2H, d, J=4.0 Hz), 4.27(2H, d, J=6.0 Hz), 4.85–4.95(1H, m), 5.98(1H, t, J=6.0 Hz), 6.14(1H, t, J=4.0 Hz), 6.55(1H, d, J=7.6 Hz), 6.80–7.16(6H, m) ppm.
d  1.25(3H, t, J=7.0 Hz), 1.40–1.60(1H, m), 1.85–2.20(3H, m), 2.04 (3H, s), 2.45(2H, t, J=6.27 Hz), 2.65–3.10(3H, m), 3.30–3.50(2H, m), 4.00–4.20(4H, m), 4.90–5.00(1H, m), 5.50–5.70(2H, m), 6.50–7.20(7H, m) ppm.
e  1.20–1.45(1H, m), 1.65–2.05(3H, m), 1.95(3H, s), 2.05–2.25(2H, m), 2.50–3.00(3H, m), 3.00–3.20(2H, m), 3.85–4.05(2H, m), 4.65–4.90 (1H, m), 5.80–6.20(1H, brs), 6.40–7.20(9H, m) ppm.

Example 29

In Vitro Biological Characterisation

The compounds of the invention are selective agonists at the $V_2$ receptor. In standard radio-ligand displacement assays, the compounds all give $K_i$ values below 10 μM for the $V_2$ receptor.

Example 30

In Vivo Biological Characterisation

The Brattleboro rat is a recognised model for vasopressin deficiency (for a review see F D Grant, "Genetic models of vasopressin deficiency", Exp. Physiol. 85, 203S–209S, 2000). The animals do not secrete vasopressin and consequently produce large volumes of dilute urine. Compounds of the invention were administered to Brattleboro rats (0.1–10 mg/kg p.o. in methylcellulose. Urine was collected hourly and volumes were compared with control animals. Animals had free access to food and water throughout the experiment. Representative results are given in the Table. Results for Desmopressin are given for comparison.

| Compound of Example | Dose | % inhibition of urine output (at 1 hour) |
|---|---|---|
| 5 | 1 mg/kg | 74 |
| 6 | 1 mg/kg | 38 |
| 8 | 1 mg/kg | 45–82 |
| 25 | 1 mg/kg | 58 |
|  | 0.1 mg/kg | 37 |
| Desmopressin | 1 mg/kg | 100 |
|  | 10 mg/kg | 100 |

Example 31

Pharmaceutical Composition for Tablet

Tablets containing 100 mg of the compound of Example 5 as the active agent are prepared from the following:

| | |
|---|---|
| Compound of Example 5 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 5.

The foregoing Examples demonstrate that compounds within the scope of the invention are readily prepared using standard chemical techniques, and that these compounds have the biological properties that would be expected of $V_2$ receptor agonists. In particular, the compounds are potent antidiuretics in an animal model of vasopressin deficiency. Thus it is clear that they may be useful in the treatment of human diseases that are currently treatable with Desmopressin, such as central diabetes insipidus, nocturnal enuresis and nocturia. It has further been suggested that antidiuretics such as Desmopressin may be useful in certain types of urinary incontinence. These arguments would also extend to the compounds of the present invention.

Desmopressin is also used in the treatment of certain coagulation disorders. There is good evidence to suggest that this action is also mediated through the $V_2$ receptor (see for example J E Kaufmann et al., "Vasopressin-induced von Willebrand factor secretion from endothelial cells involves $V_2$ receptors and cAMP", J. Clin. Invest. 106, 107–116, 2000; A Bernat et al., "$V_2$ receptor antagonism of DDAVP-induced release of hemostasis factors in conscious dogs", J. Pharmacol. Exp. Ther. 282, 597–602, 1997), and hence it would be expected that the compounds of the present invention should be useful pro-coagulants.

The scope of the present invention is further defined in the following Claims.

What is claimed is:

1. A compound of general formula 1 or a pharmaceutically acceptable salt thereof:

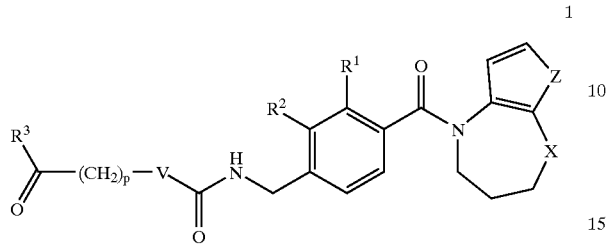

wherein:
V is a covalent bond or NH,
X is selected from $CH_2$, O and N-alkyl,
Z is either S or —CH=CH—,
$R^1$ and $R^2$ are independently selected from H, F, Cl, Br and alkyl,
$R^3$ is selected from OH, O-alkyl and $NR^4R^5$,
$R^4$ and $R^5$ are each independently H or alkyl, or together are —$(CH_2)_q$—,
p is 0, 1, 2, 3 or 4, and
q is 4 or 5.

2. A compound or salt according to claim 1 wherein Z is —CH=CH—.

3. A compound or salt according to claim 1 wherein Z is S.

4. A compound or salt according to claim 1 wherein X is $CH_2$.

5. A compound or salt according to claim 1 wherein $R^1$ is H and $R^2$ is selected from methyl and Cl.

6. A compound or salt according to claim 1 wherein $R^1$ is selected from methyl and Cl and $R^2$ is H.

7. A compound or salt according to claim 1 wherein $R^3$ is O-alkyl.

8. A compound according to claim 1 selected from:

1-(4-[N-(4-methoxy-4-oxobutanoyl)aminomethyl]-3-methylbenzoyl)-2,3,4,5-tetrahydro-1H-1-benzazepine,
1-(4-[N-(2-methoxy-2-oxoethanoyl)aminomethyl]-3-methylbenzoyl)-2,3,4,5-tetrahydro-1H-1-benzazepine,
1-(4-[N-(2-hydroxy-2-oxoethanoyl)aminomethyl]-3-methylbenzoyl)-2,3,4,5-tetrahydro-1H-1-benzazepine,
1-(4-[N-(5-methoxy-5-oxopentanoyl)aminomethyl]-3-methylbenzoyl)-2,3,4,5-tetrahydro-1H-1-benzazepine,
1-(4-[N-(2-ethoxy-2-oxoethylcarbamoyl)aminomethyl]-3-methylbenzoyl)-2,3,4,5-tetrahydro-1H-1-benzazepine,
1-(4-[N-(2-hydroxy-2-oxoethylcarbamoyl)aminomethyl]-3-methylbenzoyl)-2,3,4,5-tetrahydro-1H-1-benzazepine,
1-(3-methyl-4-[N-(2-methylamino-2-oxoethylcarbamoyl)aminomethyl]benzoyl)-2,3,4,5-tetrahydro-1H-1-benzazepine,
1-(4-[N-(2-dimethylamino-2-oxoethylcarbamoyl)aminomethyl]-3-methylbenzoyl)-2,3,4,5-tetrahydro-1H-1-benzazepine,
1-(4-[N-(2-methoxy-2-oxoethylcarbamoyl)aminomethyl]-3-methylbenzoyl)-2,3,4,5-tetrahydro-1H-1-benzazepine,
1-(4-[N-(2-amino-2-oxoethylcarbamoyl)aminomethyl]-3-methylbenzoyl)-2,3,4,5-tetrahydro-1H-1-benzazepine,
4-(3-chloro-4-[N-(4-methoxy-4-oxobutanoyl)aminomethyl]benzoyl)-5,6,7,8-tetrahydro-4H-thieno[3,2-b]azepine,
5-(4-[N-(4-methoxy-4-oxobutanoyl)aminomethyl]benzoyl)-2,3,4,5-tetrahydro-1,5-benzoxazepine,
1-(4-[N-(2-ethoxy-2-oxoethylcarbamoyl)aminomethyl]-3-methylbenzoyl)-5-methyl-2,3,4,5-tetrahydro-1H-1,5-benzodiazepine,
1-(4-[N-(3-methoxy-3-oxopropanoyl)aminomethyl]-3-methylbenzoyl)-2,3,4,5-tetrahydro-1H-1-benzazepine,
1-(4-[N-(3-ethoxy-3-oxopropanoyl)aminomethyl]-3-methylbenzoyl)-2,3,4,5-tetrahydro-1H-1-benzazepine,
1-(4-[N-(3-hydroxy-3-oxopropanoyl)aminomethyl]-3-methylbenzoyl)-2,3,4,5-tetrahydro-1H-1-benzazepine,
1-(4-[N-(4-hydroxy-4-oxobutanoyl)aminomethyl]-3-methylbenzoyl)-2,3,4,5-tetrahydro-1H-1-benzazepine,
1-(4-[N-(5-hydroxy-5-oxopentanoyl)aminomethyl]-3-methylbenzoyl)-2,3,4,5-tetrahydro-1H-1-benzazepine,
1-(4-[N-(3-methoxy-3-oxopropanoyl)aminomethyl]-2-methylbenzoyl)-2,3,4,5-tetrahydro-1H-1-benzazepine,
1-(4-[N-(N-'-ethoxycarbonylcarbamoyl)aminomethyl]-3-methylbenzoyl)-2,3,4,5-tetrahydro-1H-1-benzazepine,
1-(4-[N-(2-ethoxy-2-oxoethylcarbamoyl)aminomethyl]-2-methylbenzoyl)-2,3,4,5-tetrahydro-1H-1-benzazepine,
1-(4-[N-(2-isopropoxy-2-oxoethylcarbamoyl)aminomethyl]-3-methylbenzoyl)-2,3,4,5-tetrahydro-1H-1-benzazepine,
1-(4-[N-(2-tert-butoxy-2-oxoethylcarbamoyl)aminomethyl]-3-methylbenzoyl)-2,3,4,5-tetrahydro-1H-1-benzazepine,
1-(3-chloro-4-[N-(2-dimethylamino-2-oxoethylcarbamoyl)aminomethyl]benzoyl)-2,3,4,5-tetrahydro-1H-1-benzazepine,
1-(3-methyl-4-[N-(2-(1-piperidino)-2-oxoethylcarbamoyl)aminomethyl]benzoyl)-2,3,4,5-tetrahydro-1H-1-benzazepine,
1-(3-methyl-4-[N-(2-(1-pyrrolidino)-2-oxoethylcarbamoyl)aminomethyl]benzoyl)-2,3,4,5-tetrahydro-1H-1-benzazepine,
1-(4-[N-(3-ethoxy-3-oxopropylcarbamoyl)aminomethyl]-3-methylbenzoyl)-2,3,4,5-tetrahydro-1H-1-benzazepine, and
1-(4-[N-(3-hydroxy-3-oxopropylcarbamoyl)aminomethyl]-3-methylbenzoyl)-2,3,4,5-tetrahydro-1H-1-benzazepine or a salt thereof.

9. A pharmaceutical composition which contains active agent selected from compounds and pharmaceutically acceptable salts according to claim 1.

10. A pharmaceutical composition according to claim 9, which composition is to be used for the treatment of polyuria.

11. A pharmaceutical composition according to claim 9, which composition is to be used for the control of urinary incontinence.

12. A pharmaceutical composition according to claim 9, which composition is to be used for voiding postponement.

13. A pharmaceutical composition according to claim 9, which composition is to be used for the treatment of bleeding disorders.

14. A method of treatment of nocturnal enuresis, nocturia and diabetes insipidus, which method comprises the administration to a person in need of such treatment of an effective amount of a composition according to claim 9.

15. A method for the control of urinary incontinence, which method comprises the administration to a person in need of such treatment of an effective amount of a composition according to claim 9.

16. A method according to claim 15 wherein the treatment results in voiding postponement.

17. A method for the treatment for bleeding disorders, which method comprises the administration to a person in need of such treatment of an effective amount of a composition according to claim 9.

* * * * *